(12) United States Patent
Valentine, Jr. et al.

(10) Patent No.: US 12,251,109 B2
(45) Date of Patent: Mar. 18, 2025

(54) HANDHELD ELECTROMECHANICAL SURGICAL SYSTEM

(71) Applicant: Covidien LP, Mansfield, MA (US)

(72) Inventors: David E. Valentine, Jr., Hamden, CT (US); Alexander J. Hart, Tolland, CT (US); Charles R. Kollar, Washington, DC (US); Haley E. Strassner, Hamden, CT (US); James P. Delbo, Danville, PA (US); Steven H. Joyce, Durham, CT (US); Stephen R. Casey, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/266,200

(22) PCT Filed: Dec. 12, 2021

(86) PCT No.: PCT/US2021/061844
§ 371 (c)(1),
(2) Date: Jun. 8, 2023

(87) PCT Pub. No.: WO2022/125397
PCT Pub. Date: Jun. 16, 2022

(65) Prior Publication Data
US 2024/0023967 A1    Jan. 25, 2024

Related U.S. Application Data

(60) Provisional application No. 63/122,538, filed on Dec. 8, 2020.

(51) Int. Cl.
*A61B 17/064* (2006.01)
*A61B 17/115* (2006.01)
(Continued)

(52) U.S. Cl.
CPC .......... *A61B 17/1155* (2013.01); *A61B 90/06* (2016.02); *A61B 2017/00119* (2013.01);
(Continued)

(58) Field of Classification Search
CPC .................................................. A61B 17/1155
See application file for complete search history.

(56) References Cited

U.S. PATENT DOCUMENTS 11,744,592 B2 * 9/2023 Mozdzierz ......... A61B 17/1155
227/179.1
2019/0245854 A1   8/2019 Saito
(Continued)

FOREIGN PATENT DOCUMENTS

EP    2777518 A1    9/2014
EP    3403590 A1    11/2018
(Continued)

OTHER PUBLICATIONS

International Search Report for Application No. PCT/US2021/061844 dated Mar. 14, 2022.
(Continued)

*Primary Examiner* — Eyamindae C Jallow

(57) ABSTRACT

A surgical device includes a handle assembly having a power source; a motor coupled to the power source; and a controller configured to control the motor. The surgical device also includes an adapter assembly configured to selectively couple to the handle assembly; a reload configured to selectively couple to a distal portion of the adapter assembly, the reload including a plurality of fasteners; and an anvil assembly selectively couplable to the distal portion of the adapter assembly, the anvil assembly being movable relative to the reload. The controller is further configured to control the motor to move the anvil assembly from a starting position to a compressed position thereby compressing
(Continued)

tissue at a target clamping force between the anvil assembly and the reload.

17 Claims, 8 Drawing Sheets

(51) Int. Cl.
*A61B 90/00* (2016.01)
*A61B 17/00* (2006.01)
(52) U.S. Cl.
CPC ............... *A61B 2017/00199* (2013.01); *A61B 2017/00398* (2013.01); *A61B 2017/00734* (2013.01); *A61B 2090/064* (2016.02); *A61B 2090/0811* (2016.02)

(56) References Cited

U.S. PATENT DOCUMENTS

2020/0246011 A1\* 8/2020 Sgroi, Jr. ........... A61B 17/1155
2020/0315623 A1\* 10/2020 Eisinger ........... A61B 17/07207

FOREIGN PATENT DOCUMENTS

EP       3412225 A1 \* 12/2018  ............ A61B 17/00
WO    2020014056 A1    1/2020

OTHER PUBLICATIONS

Written Opinion for Application No. PCT/US2021/061844 dated Mar. 14, 2022.

\* cited by examiner

HANDHELD ELECTROMECHANICAL SURGICAL SYSTEM

CROSS-REFERENCE TO RELATED APPLICATIONS

This application claims the benefit of U.S. Provisional Patent Application No. 63/122,538, filed Dec. 8, 2020, the entire contents of which are incorporated by reference herein.

1. TECHNICAL FIELD

The present disclosure relates to surgical devices. More specifically, the present disclosure relates to handheld electromechanical surgical systems for performing surgical procedures.

2. BACKGROUND OF RELATED ART

One type of surgical device is a circular clamping, cutting and stapling device. Such a device may be employed in a surgical procedure to reattach rectum portions that were previously transected, or similar procedures. Conventional circular clamping, cutting and stapling instruments include a pistol or linear grip-styled structure having an elongated shaft extending therefrom and a staple cartridge supported on the distal end of the elongated shaft. In this instance, a physician may insert an anvil assembly of the circular stapling instrument into a rectum of a patient and maneuver the anvil assembly up the colonic tract of the patient toward the transected rectum portions. The physician may also insert the remainder of the circular stapling instrument (including the cartridge assembly) through an incision and toward the transected rectum portions. The anvil and cartridge assemblies are approximated toward one another and staples are ejected from the cartridge assembly toward the anvil assembly to form the staples in tissue to affect an end-to-end anastomosis, and an annular knife is fired to core a portion of the clamped tissue portions. After the end-to-end anastomosis has been effected, the circular stapling apparatus is removed from the surgical site.

A number of surgical device manufacturers have developed product lines with proprietary powered drive systems for operating and/or manipulating the surgical device. In many instances the surgical devices include a powered handle assembly, which is reusable, and a disposable staple cartridge assembly, end effector or the like that is selectively connected to the powered handle assembly prior to use and then disconnected from the staple cartridge assembly or end effector following use in order to be disposed of or in some instances sterilized for re-use.

Powered electromechanical surgical staplers, including battery power sources, utilize motors to actuate various components of the powered surgical stapler during clamping, stapling, and cutting portions of the anastomosis procedure. Thus, there is a need for a powered surgical stapler configured for precise control of the motors during these phases to form a leak-proof anastomosis.

SUMMARY

A powered circular stapler according to the present disclosure is used to create anastomoses on a variety of tissue types, thicknesses, and disease states across multiple surgical techniques. Depending on the tissue type, thickness, etc., the force required to approximate the tissue that forms the anastomosis may vary between procedures. In situations where the tissue is particularly thick or dense due to tissue type or condition, clamping at the same speed and force as for thinner tissue could result in tissue trauma, over compression, or an inability to compress tissue to a desired tissue gap.

The presently described powered circular stapler is configured to clamp tissue to reach a target clamping pressure in order to reduce trauma during clamping and allow fluids in the tissue to leave the site atraumatically. If the powered circular stapler is unable to reach the desired tissue gap at this target pressure, the user may still want to create an anastomosis with this tissue. Unlike conventional staplers, which require removal of the stapler and re-insertion with a larger reload/anvil, the present powered circular stapler is configured to achieve the desired tissue gap.

This present disclosure provides a controlled tissue compression ("CTC") algorithm that controls clamping when the force required to achieve full clamping exceeds the targeted clamping pressure during a controlled tissue compression phase of a clamping algorithm. In this case, the pressure applied by the powered circular stapler to the tissue is increased proportionally to the distance required to reach a desired tissue gap. The pressure is increased continuously and proportionally until the desired tissue gap is achieved or a timeout is triggered. The user may also continue clamping after timeout until the desired tissue gap is achieved. During the compression phase, the pressure is increased until a pressure limit value is reached, at which point the pressure remains constant until the desired tissue gap is achieved or timeout occurs.

According to one embodiment of the present disclosure, a surgical device is disclosed. The surgical device includes a handle assembly having a power source; a motor coupled to the power source; and a controller configured to control the motor. The surgical device also includes an adapter assembly configured to selectively couple to the handle assembly; a reload configured to selectively couple to a distal portion of the adapter assembly, the reload including a plurality of fasteners; and an anvil assembly selectively couplable to the distal portion of the adapter assembly, the anvil assembly being movable relative to the reload. The controller is further configured to control the motor to move the anvil assembly from a starting position to a compressed position thereby compressing tissue at a target clamping force between the anvil assembly and the reload.

According to one aspect of the above embodiment, the reload may include a storage device storing a starting clamping force and a maximum force value. The controller may be further configured to communicate with the storage device and set the target clamping force to the starting clamping force. The controller may be further configured to determine a current position of the anvil assembly and a distance traveled by the anvil assembly. The controller may be further configured to perform a comparison of at least one of the distance traveled to a minimum distance or the current position to the compressed position. The controller may be further configured to increment the target clamping force by a change in force value in response to the comparison.

According to another aspect of the above embodiment, the controller may be further configured to calculate the change in force value based on a distance ratio. The controller may be further configured to calculate the distance ratio by dividing a first distance difference and a second distance difference. The controller may be further configured to calculate the first distance difference between the current position of the anvil assembly and the compressed position.

The controller may be further configured to calculate the second distance difference between the starting position to the compressed position. The controller may be further configured to calculate the change in force value by multiplying the distance ratio and the maximum force value. The controller may be further configured to determine whether the anvil assembly reached the compressed position within a set time period.

According to another embodiment of the present disclosure, a surgical device is disclosed. The surgical device includes a handle assembly having a power source; a motor coupled to the power source; and a controller configured to control the motor. The surgical device also includes an adapter assembly configured to selectively couple to the handle assembly; a reload configured to selectively couple to a distal portion of the adapter assembly, the reload including a plurality of fasteners; and an anvil assembly selectively couplable to the distal portion of the adapter assembly, the anvil assembly being movable relative to the reload. The controller is further configured to control the motor to move the anvil assembly from a starting position to a compressed position thereby compressing tissue at a target clamping force between the anvil assembly and the reload within a set time period. The controller is also configured to determine whether the anvil assembly reached the compressed position within a set time period; perform a comparison of at least one of a distance traveled by the anvil assembly to a minimum distance or a current position of the anvil assembly to the compressed position; and increment the target clamping force by a change in force value based on the comparison.

According to one aspect of the above embodiment, the reload may include a storage device storing a starting clamping force and a maximum force value. The controller may be further configured to communicate with the storage device and set the target clamping force to the starting clamping force. The controller may be further configured to calculate the change in force value based on a distance ratio.

According to another aspect of the above embodiment, the controller may be further configured to calculate the distance ratio by dividing a first distance difference and a second distance difference. The controller may be further configured to calculate the first distance difference between the current position of the anvil assembly and the compressed position. The controller may be further configured to calculate the second distance difference between the starting position to the compressed position. The controller may be further configured to calculate the change in force value by multiplying the distance ratio and the maximum force value.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
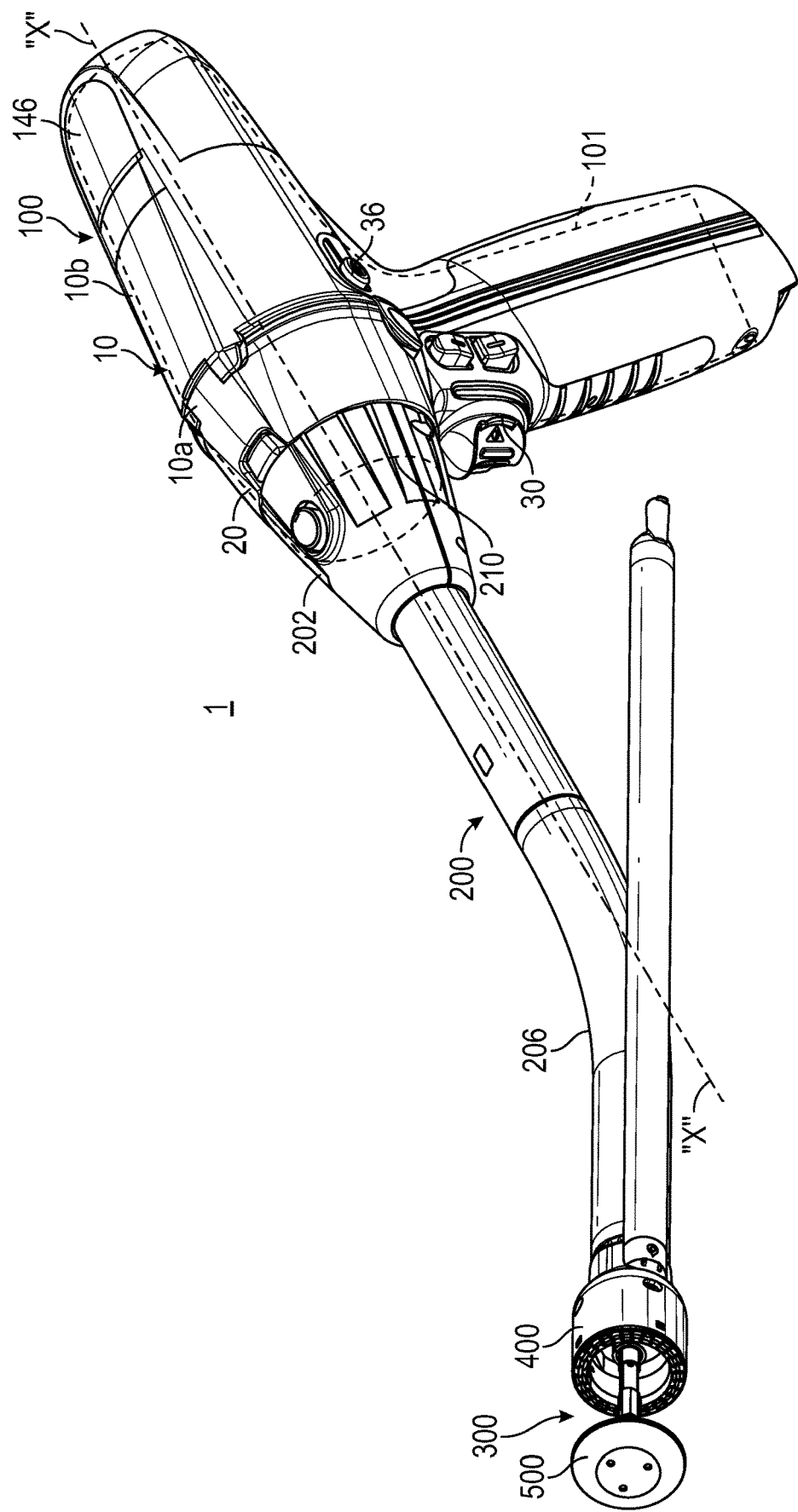
FIG. 1 is a perspective view of a handheld surgical instrument including a handle assembly, an adapter assembly, and an end effector, in accordance with an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical instrument, such as, for example, a powered circular stapler 1 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 (FIG. 2) and an outer shell housing 10 configured to selectively receive and encase power handle 101. The shell housing 10 includes a distal half-section 10a and a proximal half-section 10b pivotably connected to distal half-section 10a. When joined, distal and proximal half-sections 10a, 10b define a shell cavity therein in which power handle 101 is disposed.

Distal and proximal half-sections 10a, 10b of shell housing 10 are divided along a plane that traverses a longitudinal axis "X" of adapter assembly 200. Distal half-section 10a of shell housing 10 defines a connecting portion 20 configured to accept a corresponding drive coupling assembly 210 (FIG. 3) of adapter assembly 200, which includes an electrical connector 312. Distal half-section 10a of shell housing 10 supports a toggle control button 30. Toggle control button 30 is capable of being actuated in four directions (e.g., a left, right, up and down).

Figure 2:
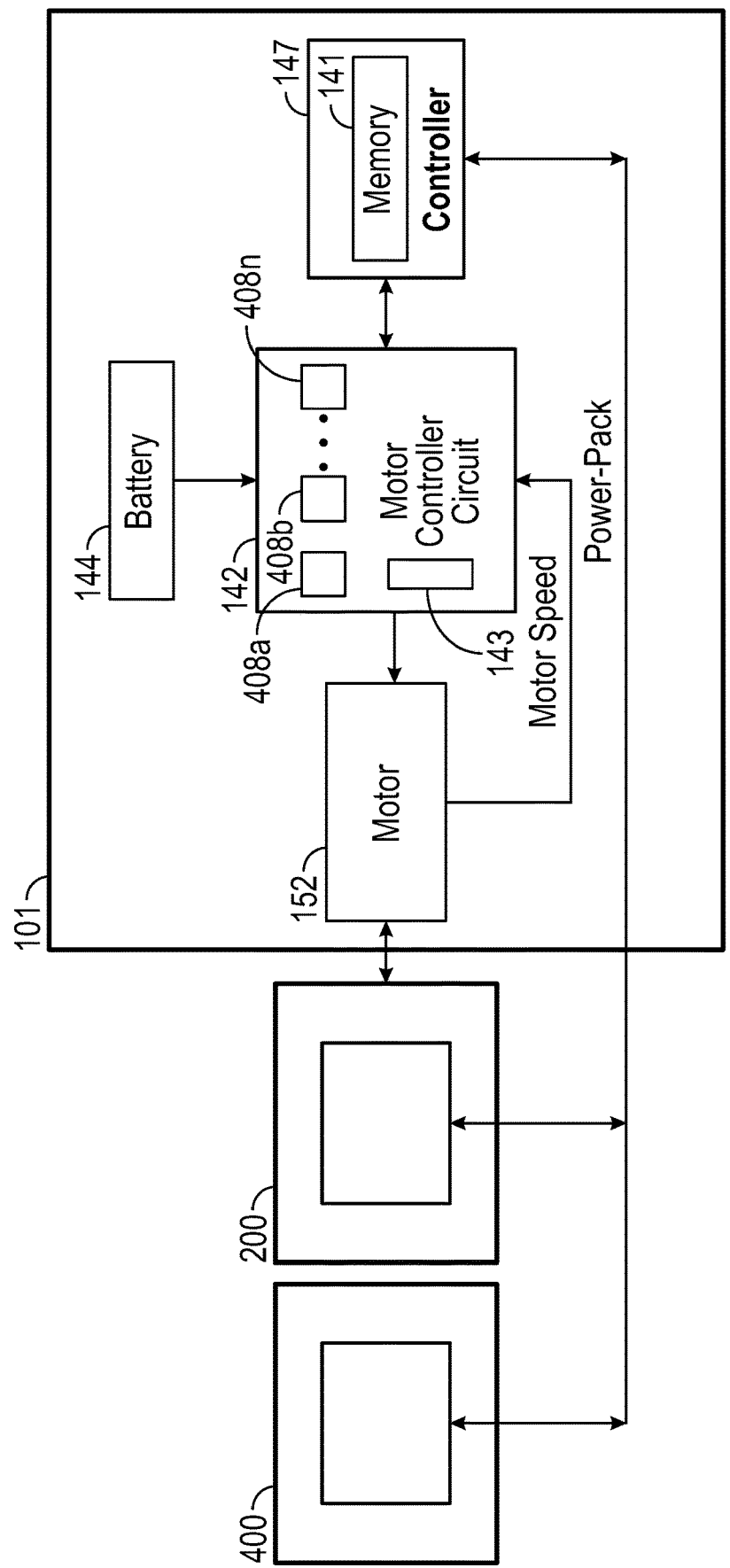
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a motor 152 coupled to the battery 144. The power handle 101 also includes a display screen 146. In embodiments, the motor 152 may be coupled to any suitable power source configured to provide electrical energy to the motor 152, such as an AC/DC transformer. The battery 144 and the motor 152 are coupled to the main controller circuit board 142 having a motor controller 143 which controls the operation of the motor 152 including the flow of electrical energy from the battery 144 to the motor 152. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a . . . 408n configured to measure operational states of the motor 152 and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. The position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motor 152.

The motor controller 143 is coupled to the main controller 147, which includes a plurality of inputs and outputs for interfacing with the motor controller 143. In particular, the main controller 147 receives measured sensor signals from the motor controller 143 regarding operational status of the motor 152 and the battery 144 and, in turn, outputs control signals to the motor controller 143 to control the operation of the motor 152 based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

In addition to motor 152, the power handle 101 may further include one or more additional motors each electrically connected to a main controller circuit board 142 and battery 144. Each motor, including the motor 152, includes a respective motor shaft (not explicitly shown) extending therefrom. Rotation of the motor shafts by the respective motors function to drive shafts and/or gear components of adapter assembly 200 in order to perform the various operations of handle assembly 100. In particular, motors, i.e., motor 152, of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fires an annular array of staples of reload 400, and moves an annular knife (not explicitly shown) of reload 400.

Figure 3:
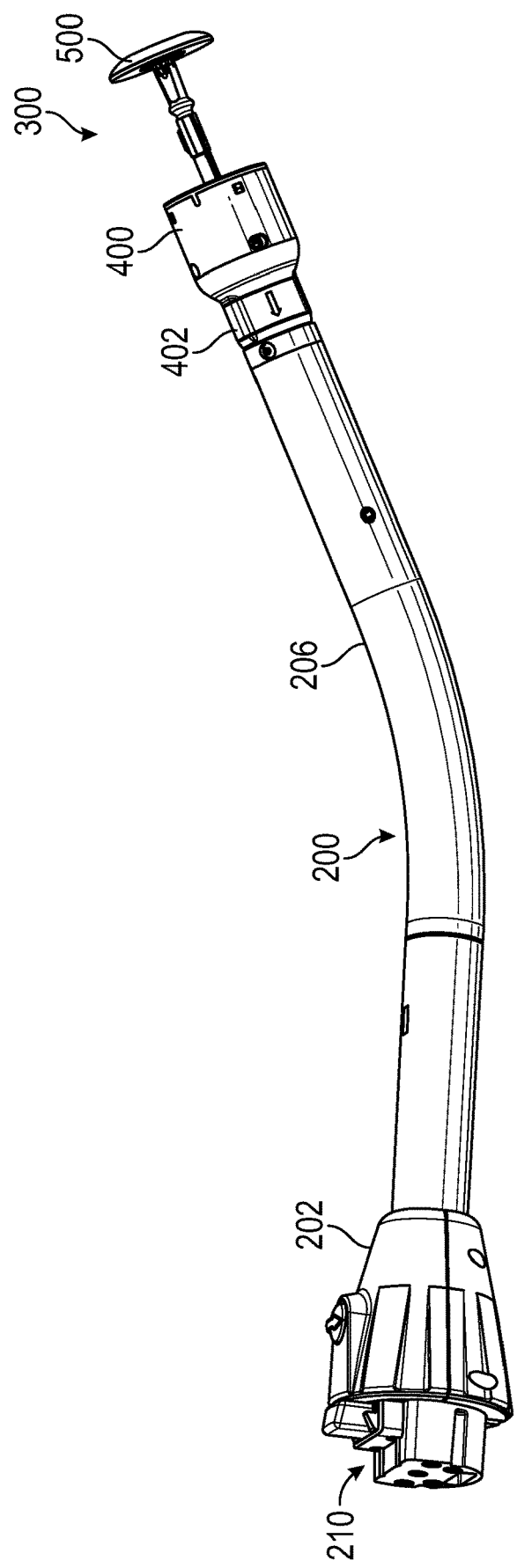
FIG. 3 is a side perspective view of the adapter assembly and the end effector (e.g., an annular reload and an anvil assembly) attached to the adapter assembly.
Figure 4:
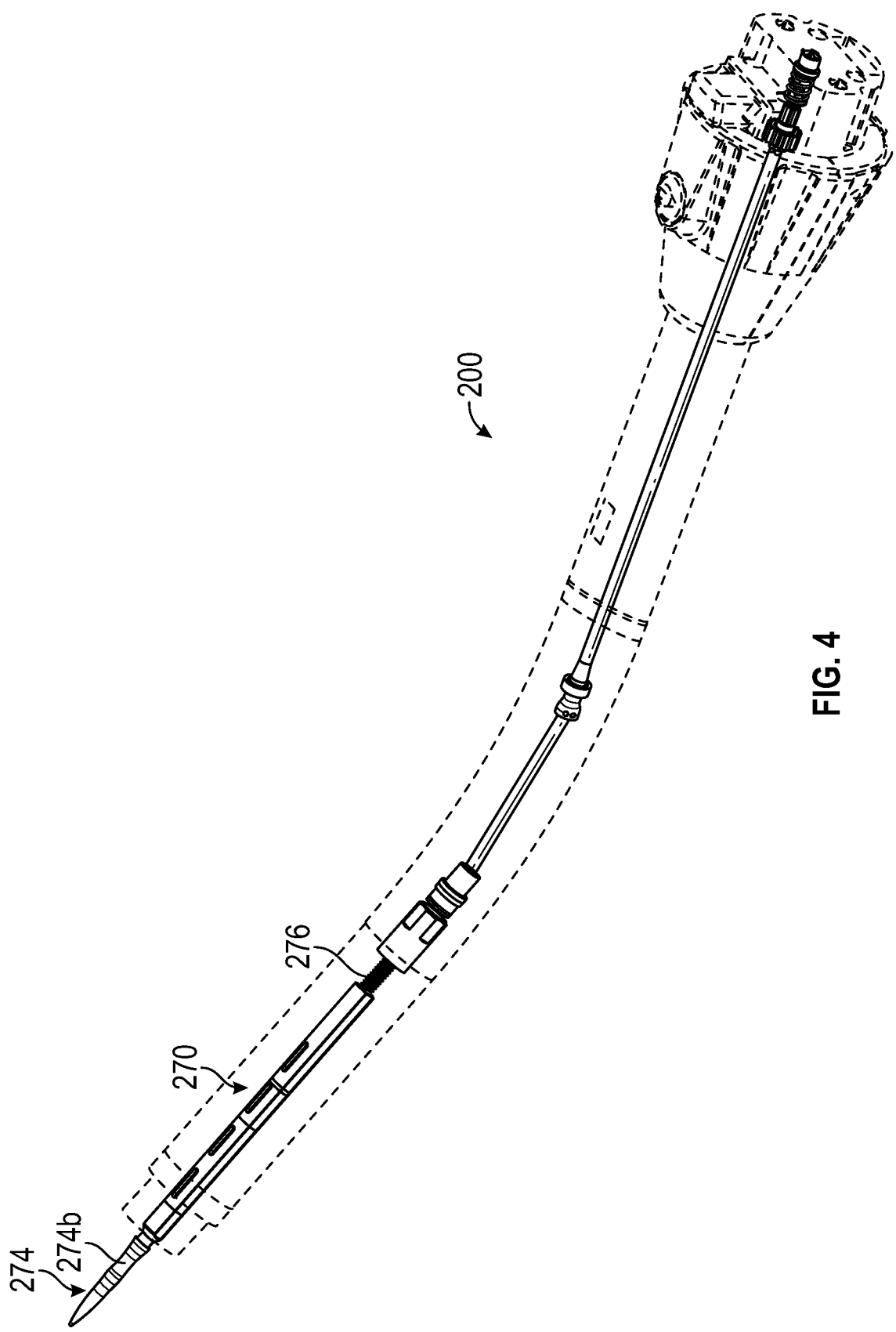
FIG. 4 is a perspective view of the adapter assembly, shown partially in phantom, without the end effector (e.g., the annular reload and the anvil assembly)

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver assembly (not explicitly shown) or knife assembly (not explicitly shown) of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

The strain gauge 408b of adapter assembly 200 measures and monitors the retraction of trocar member 274. During the closing of end effector 300, when anvil assembly 500 contacts tissue, an obstruction, a tissue-contacting surface of the reload 400, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics (FIG. 8) are then displayed on the display screen 146 of handle assembly 100 to provide the user with real-time information related to the status of the firing of handle assembly 100.

Figure 5:
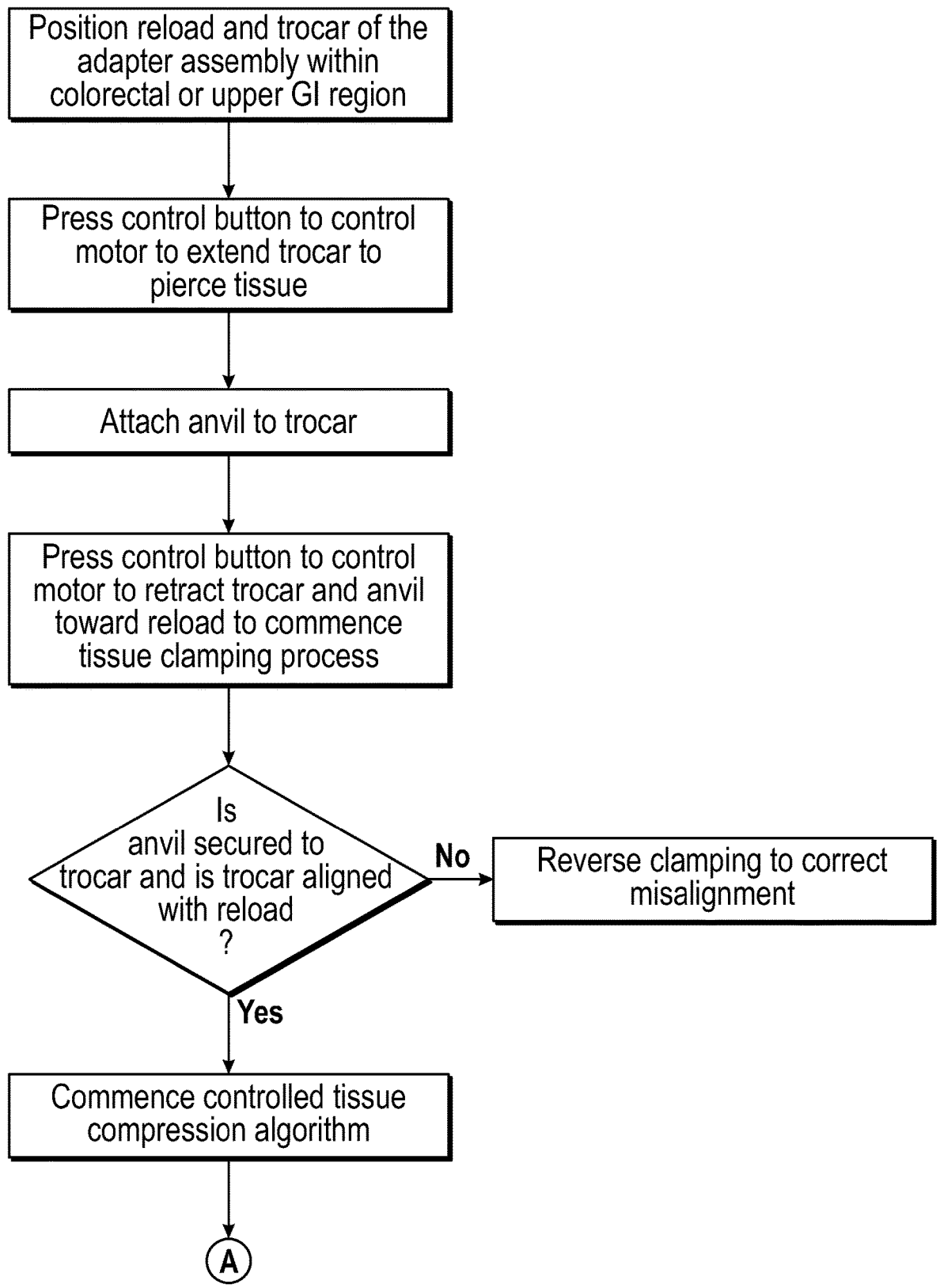
FIG. 5 is a flow chart of a method for performing a stapling function of the surgical instrument of FIG. 1 according to an embodiment of the present disclosure.

The trocar assembly 270 is axially and rotationally fixed within outer tube 206 of adapter assembly 200. With reference to FIG. 5, adapter assembly 200 includes a support block 292 fixedly disposed within outer tube 206. The adapter assembly 200 also includes a strain gauge assembly 408b, which is disposed between the support block 292 and a connector sleeve 292. The reload 400 is removably coupled to the support block 292.

In operation, strain gauge assembly 408b of adapter assembly 200 measures and monitors the retraction of trocar member 274, which passes through the strain gauge assembly 408b. During the closing of reload 400, if and when anvil assembly 500 contacts tissue, an obstruction, staple cartridge 420 or the like, a reaction force is exerted on anvil assembly 500 which is in a generally distal direction. This distally directed reaction force is communicated from anvil assembly 500 to the trocar assembly 270, which in turn then transmits the force to support block 292. Support block 292 then communicates the distally directed reaction force to a strain sensor of the strain gauge assembly 408b.

Strain sensor of strain gauge assembly 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge assembly 408b provides a closed-loop feedback to a firing/clamping load exhibited by first, second and third force/rotation transmitting/converting assemblies.

Strain sensor of strain gauge assembly 408b then communicates signals to main controller circuit board 142. Graphics are then displayed on display screen 146 of powerpack core assembly 106 of handle assembly 100 to provide the user with real-time information related to the status of the firing of handle assembly 100. Strain gauge assembly 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

During operation, the anvil assembly 500 (already positioned by surgeon) is attached to the trocar member 274 and the user begins the clamping process on the tissue interposed between reload 400 and the anvil assembly 500 by pressing on the bottom of the toggle control button 30. During clamping, the anvil assembly 500 is retracted toward the reload 400 until reaching a preset, fully clamped position, namely a position of the anvil assembly 500 at which the tissue is fully clamped between the anvil assembly 500 and the reload 400. The preset, fully clamped position varies for each of the different types of reloads (e.g., the distance is about 29 mm for 25 mm reloads). While clamping, the strain gauge 408b continuously provides measurements to the main controller 147 on the force imparted on the trocar member 274 as it moves the anvil assembly 500 to clamp tissue between the anvil assembly 500 and the reload 400.

With reference to FIG. 5, the user commences a surgical procedure by positioning the adapter assembly 200, including the trocar member 274 and the anvil assembly 510, within the colorectal or upper gastrointestinal region. The user presses the toggle control button 30 to extend the trocar member 274 until it pierces tissue. After extension of the trocar member 274, the anvil assembly 510 that was previously positioned by surgeon is attached to the trocar member 274 and the user begins the clamping process on the tissue interposed between reload 400 and the anvil assembly 510 by pressing on the bottom portion of the toggle control button 30.

Figure 6:
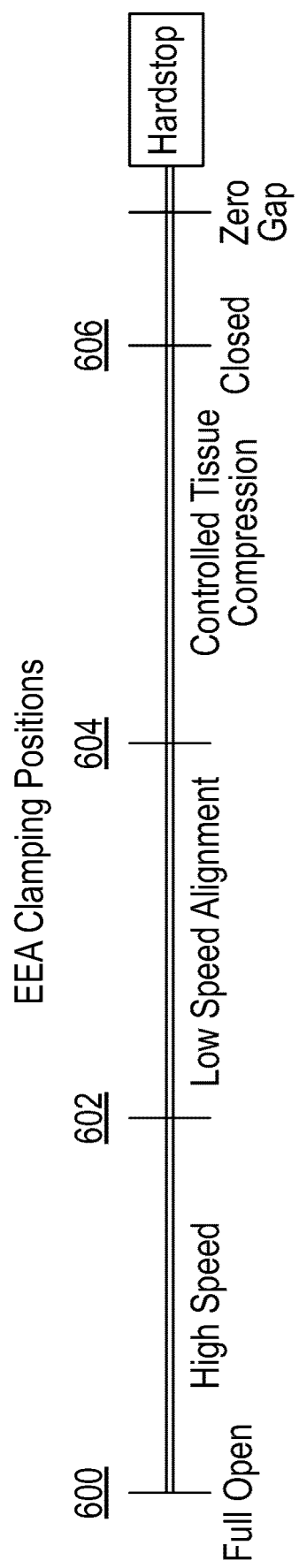
FIG. 6 is a schematic diagram illustrating travel distance and speed of the anvil assembly during a clamping sequence performed by the surgical instrument of FIG. 1 according to an embodiment of the present disclosure.

During clamping, the anvil assembly 510 is retracted toward the reload 400. With reference to FIG. 6, the anvil assembly 510 is initially retracted from a full open position 600 at a first speed for a first segment from the full open position 600 to a first distance 602. Thereafter, the anvil assembly 510 traverses a second distance from the first distance 602 to a second distance 604 at the second speed, which is slower than the first speed. As the anvil assembly 510 is traversing the second segment, the main controller 147 continuously verifies whether the measured force is within predefined parameters to determine if the measured force exceeds a high force threshold limit. This measurement is used to detect misalignment of trocar member 274 with the reload 400. If the force is higher than the high force threshold, then the power handle 101 temporarily reverses the rotation transmitting assembly 240 to retract the anvil assembly in an attempt to correct the misalignment of trocar member 274 with the reload 400. The main controller 147 then reattempts to continue clamping until a third distance 604 is reached, which is a starting position for the CTC algorithm. If the third distance 604 is not reached within a predetermined period of time, the main controller 147 then issues an error, including an alarm on the display screen 146 prompting the user to inspect the anvil assembly 510. After inspection and clearance of any obstruction, the user may then restart the clamping process.

Once the anvil assembly 510 reaches the third distance 604 at the end of the second segment, the power handle 101 performs a rotation verification to check position of the anvil assembly 510. Then the main controller commences the CTC algorithm which varies the clamping speed during tissue compression without exceeding a target compression force.

Figure 7:
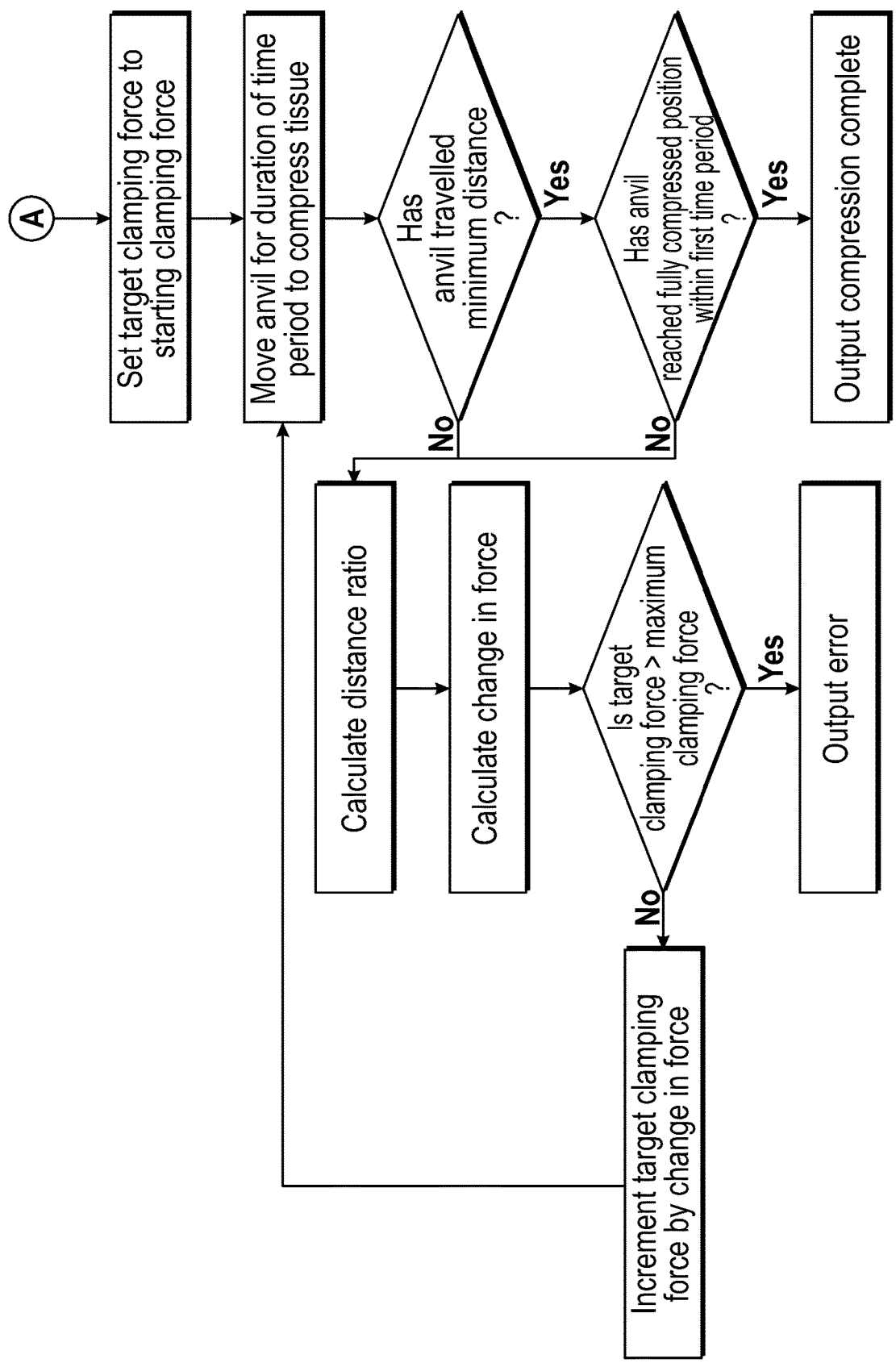
FIG. 7 is a flow chart of a method for performing a controlled tissue compression function of the surgical instrument of FIG. 1 according to an embodiment of the present disclosure.

With reference to FIG. 7, the CTC uses force exerted on tissue that is derived by the main controller 147 from the strain gauge 408b. During CTC, the user continues to press down on the toggle control button 30 to continue operation of handle assembly 100. The third distance 604, i.e., starting position for the CTC, at which the controller commences the CTC, corresponds to the distance at which the anvil assembly 510 begins to compress the tissue against the staple guide of the reload 400 for the remainder of the clamping process. CTC controls the movement of the anvil assembly 510 during a third segment, from the third distance 604 to a fourth distance 606, which corresponds to the compressed position of the anvil assembly 510. CTC continues until the anvil assembly 510 reaches the fourth distance 606. During compression, if no forces are detected, the handle assembly 100 identifies that the anvil assembly 510 is missing and the handle assembly 100 issues an error.

The CTC is run for a predetermined time period, namely, a first time period, which may be from about 30 seconds to about 180 seconds, and an optional second time period, which may be from about 30 seconds to about 120 seconds. During execution of the CTC, the main controller 147 monitors force based on strain as measured by the strain gauge 408b that is imparted on the first rotation transmitting assembly 240 as it moves the anvil assembly 510.

The reload 400 includes a storage device 402 (e.g., memory) configured to store operating parameters of the reload 400 including starting clamping force, maximum clamping force, and a force factor. The storage device 402 may be any suitable type, such as flash memory, EEPROM, and the like. Each type of reload 400 may have a corresponding starting clamping force, which the main controller 147 may obtain automatically by reading the starting clamping force value from the storage device 402 and/or set manually by the user by selecting either the type of the reload 400 or the clamping force directly. Starting clamping force may be any suitable threshold, e.g., from about 100 pounds to about 200 pounds. In embodiments, the target clamping force may be approximately 150 pounds. In embodiments, a 33 mm sized reload 400 may have a clamping force of about 150 lbs.

Initially, the main controller 147 sets starting clamping force as a target clamping force based on a size of the reload 400. During the first time period, the main controller 147 signals the motor 152 to move the anvil assembly 510 toward the reload 400. The motor 152 is rotated at a constant or variable speed that moves the anvil assembly 510 until the compressed position (i.e., fourth distance 606) is reached within the first time period.

While the anvil assembly 510 is being moved, the main controller 147 also continuously monitors the position for each sampling period, e.g., about every 100 milliseconds. The main controller 147 obtains the distance traveled by the anvil assembly 510, e.g., based on rotations of the motor 152. The main controller 147 compares the distance traveled to a minimum travel distance, e.g., about 20 rotations of the motor 152. Thus, if the main controller 147 determines that the motor 152 has not rotated for the minimum travel distance during a single sampling period, the main controller 147 increments the target clamping force using a distance ratio.

The main controller 147 calculates the distance ratio, which indicates the distance traveled by the anvil assembly 510 during the compression process. The distance ratio is calculated by dividing a first distance difference, which is a difference between the current position of the anvil assembly 510 and the fourth distance 606 (i.e., the compressed position) by a second distance difference, which is a difference between the third distance 604 and the fourth distance 606. Thus, the distance ratio is 1.0 at the start of the CTC, namely, the third distance 604 (i.e., starting position), and the distance ratio is 0.0 at the of the CTC, namely, the fourth distance 606 (i.e., the compressed position).

The main controller 147 also calculates a change in force by calculating a force difference between the maximum clamping force (i.e., obtained from the storage device 402) and the target clamping force. The maximum clamping force indicates the maximum clamping force that can be applied to the reload 400 during tissue compression. The maximum clamping force may be about 150% of the starting clamping force and in embodiments may be from about 150 lbs. to about 300 lbs., and may be about 225 lbs. for a 33 mm reload 400. The main controller 147 then multiplies the force difference by the distance ratio and the force factor also obtained from the storage device 402 to calculate the change in force. The force factor is a parameter designed to mediate the change in force. The force factor may be calculated to be specific to each specific size and type of the reload 400. The current target clamping force is then incremented by the change in force.

Figure 8:
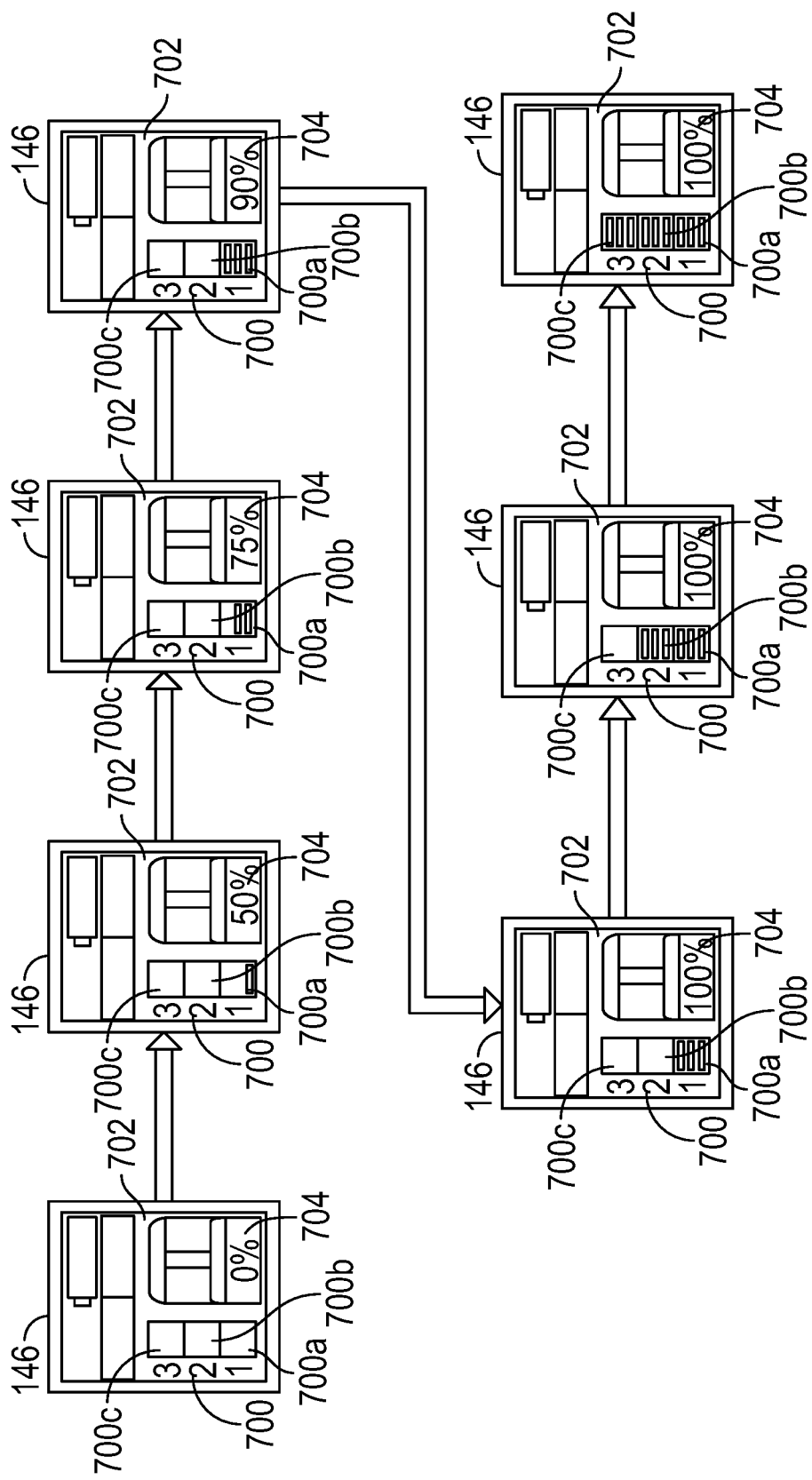
FIG. 8 are images displayed on a display screen of the surgical instrument of FIG. 1 during execution of controlled tissue compression function according to an embodiment of the present disclosure.

With reference to FIG. 8, a sequence of images displayed on the display screen 146 during CTC is shown. Once CTC is commenced, the display screen 146 displays a CTC user interface after the main controller 147 confirms that the anvil assembly 510 is present based on detection of a minimum force. In particular, the display screen 146 shows a gauge 700 illustrating the force being imparted on the tissue and an animation 702 of the anvil assembly 510 and tissue being compressed. Also displayed is the progress percentage 704 of the clamping until the fourth distance 606 is reached. Thus, as the anvil assembly 510 is being moved to compress the tissue under the CTC, the gauge 700, the anvil animation 702, and the distance traveled by the anvil assembly 510 as progress percentage 704 are updated continuously to provide real time feedback regarding the CTC progress.

During CTC, the strain gauge 408b continuously provides measurements to the main controller 147 of the force imparted on the first rotation transmitting assembly 240 as it moves the anvil assembly 510. The force measured by the strain gauge 408b is represented by the gauge 700 on the display screen 146, which is separated into three zones, zone 700a shows the force from 0% to 50% of the starting clamping force, zone 700b shows the force from 51% to 100% of the starting clamping force, and zone 700c shows the force between the starting clamping force and the maximum clamping force. A high force caution graphic may also be displayed on screen for zone 700c.

After expiration of the first time period, the main controller 147 determines whether the anvil assembly 510 has reached the compressed position. The main controller 147 compares the distance traveled to the fourth distance 606. If the anvil assembly 510 has not reached the compressed position, the main controller 147 calculates the distance ratio and the change in force and increments the target clamping force. In both situations, the target clamping force may be incremented until the maximum force is reached. Thus, the CTC algorithm continues to compress tissue until either the compressed position or the maximum clamping force is reached. If the maximum clamping force is exceeded, an error is outputted on the display screen 146. Once the CTC algorithm is complete and tissue is compressed, handle assembly 100 activates an LED and issues a tone indicating the same and the CTC screen indicates 100% compression is continuously displayed on the display screen 146 until the stapling sequence is started.

To initiate stapling sequence, the user presses one of the safety buttons 36 of the power handle 101, which acts as a safety and arms the toggle control button 30, allowing it to commence stapling. Upon activation of the safety button 36, a second rotation verification calibration check is performed. The display screen 146 transitions to the stapling sequence display, which includes a circle illustrating an animated view of a circular anastomosis, a progress bar, and a staple icon. The stapling sequence screen is displayed until user initiates the stapling sequence, exits the stapling sequence, or unclamps. After the stapling sequence is completed, the user presses the toggle control button 30 to commence the cutting sequence to cut the stapled and compressed tissue and form the anastomosis.

The CTC algorithm according to the present disclosure allows the surgeon to clamp extremely thick tissue without overcompressing and damaging the tissue. The algorithm also allows for fluid to move out of the site and tissue to achieve the preset tissue gap in order to encourage successful staple formation. This is done by tracking the position of the trocar member 274 and calculating the ratio of current position to target position and increasing the pressure in proportion to that ratio until a pressure limit is reached. By maintaining tissue health and compressing in a more safe, controlled manner, better anastomotic health and therefore, better patient outcomes may be achieved. The algorithm also prevents delay in surgery or potentially an inability to use the product by the surgeon.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a handle assembly including:
      a power source;
      a motor coupled to the power source; and
      a controller configured to control the motor;
   an adapter assembly configured to selectively couple to the handle assembly;
   a reload configured to selectively couple to a distal portion of the adapter assembly, the reload including a plurality of fasteners; and
   an anvil assembly selectively couplable to the distal portion of the adapter assembly, the anvil assembly being movable relative to the reload to define a starting position, a current position, and a compressed position;
   wherein the controller is further configured to:
      set a target clamping force between the anvil assembly and the reload;
      control the motor to move the anvil assembly from the starting position toward the compressed position to compress tissue at the target clamping force; and
      increment the target clamping force by a change in force value, wherein the change in force value is based on a distance ratio comprising the starting position, the current position, and the compressed position.

2. The surgical device according to claim 1, wherein the reload includes a storage device storing a starting clamping force and a maximum force value.

3. The surgical device according to claim 2, wherein the controller is further configured to communicate with the storage device and set the target clamping force to the starting clamping force.

4. The surgical device according to claim 3, wherein the controller is further configured to determine the current position of the anvil assembly and a distance traveled by the anvil assembly.

5. The surgical device according to claim 4, wherein the controller is further configured to perform a comparison of at least one of the distance traveled to minimum distance, or the current position to the compressed position.

6. The surgical device according to claim 4, wherein the controller is further configured to determine whether the anvil assembly reached the compressed position within a set time period.

7. The surgical device according to claim 1, wherein the controller is further configured to calculate the distance ratio by dividing a first distance difference and a second distance difference.

8. The surgical device according to claim 7, wherein the controller is further configured to calculate the first distance difference between the current position of the anvil assembly and the compressed position.

9. The surgical device according to claim 7, wherein the controller is further configured to calculate the second distance difference between the starting position to the compressed position.

10. The surgical device according to claim 1, wherein the controller is further configured to calculate the change in force value by multiplying the distance ratio and a maximum force value.

11. A surgical device comprising:
    a handle assembly including:
       a power source;
       a motor coupled to the power source; and
       a controller configured to control the motor;
    an adapter assembly configured to selectively couple to the handle assembly;
    a reload configured to selectively couple to a distal portion of the adapter assembly, the reload including a plurality of fasteners; and
    an anvil assembly selectively couplable to the distal portion of the adapter assembly, the anvil assembly being movable relative to the reload to define a starting position, a current position, and a compressed position;
    wherein the controller is further configured to:
       set a target clamping force between the anvil assembly and the reload;
       control the motor to move the anvil assembly from the starting position to the compressed position to compress tissue at the target clamping force within a set time period;
       determine whether the anvil assembly reached the compressed position within the set time period; and
       perform a comparison of at least one of: a travel distance of the anvil assembly to a minimum travel distance, or the current position to the compressed position; and
       based on the comparison, increment the target clamping force by a change in force value, with the change in force value based on a distance ratio comprising the starting position, the current position, and the compressed position.

12. The surgical device according to claim 11, wherein the reload includes a storage device storing a starting clamping force and a maximum force value.

13. The surgical device according to claim 12, wherein the controller is further configured to communicate with the storage device and set the target clamping force to the starting clamping force.

14. The surgical device according to claim 11, wherein the controller is further configured to calculate the distance ratio by dividing a first distance difference and a second distance difference.

15. The surgical device according to claim 14, wherein the controller is further configured to calculate the first distance difference between the current position of the anvil assembly and the compressed position.

16. The surgical device according to claim 14, wherein the controller is further configured to calculate the second distance difference between the starting position to the compressed position.

17. The surgical device according to claim 14, wherein the controller is further configured to calculate the change in force value by multiplying the distance ratio and a maximum force value.

* * * * *